United States Patent
Braun et al.

(10) Patent No.: US 10,213,169 B2
(45) Date of Patent: Feb. 26, 2019

(54) AUTOMATED POSITIONING OF A PATIENT TABLE RELATIVE TO A MEDICAL INSTALLATION

(71) Applicants: Christoph Braun, Rosenheim (DE); Johann Uebler, Nürnberg (DE)

(72) Inventors: Christoph Braun, Rosenheim (DE); Johann Uebler, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 584 days.

(21) Appl. No.: 14/847,437

(22) Filed: Sep. 8, 2015

(65) Prior Publication Data

US 2016/0073979 A1 Mar. 17, 2016

(30) Foreign Application Priority Data

Sep. 16, 2014 (DE) .................. 10 2014 218 557

(51) Int. Cl.
*A61B 6/04* (2006.01)
*A61B 6/03* (2006.01)
(Continued)

(52) U.S. Cl.
CPC ............ *A61B 6/0492* (2013.01); *A61B 6/032* (2013.01); *A61B 6/0457* (2013.01); *A61B 6/461* (2013.01);
(Continued)

(58) Field of Classification Search
CPC ........ A61B 6/0492; A61B 34/25; G06F 3/048
See application file for complete search history.

(56) References Cited

U.S. PATENT DOCUMENTS 5,086,401 A * 2/1992 Glassman .............. A61B 34/20
606/53
6,314,312 B1 * 11/2001 Wessels ................. A61B 90/10
600/427
(Continued)

FOREIGN PATENT DOCUMENTS

DE 102007017794 * 12/2008
DE 102007017794 B3 12/2008

OTHER PUBLICATIONS

German Office Action for related German Application No. 10 2014 218 557.2, dated May 7, 2015, with English Translation.

*Primary Examiner* — Eric J Kurilla
(74) *Attorney, Agent, or Firm* — Lempia Summerfield Katz LLC

(57) ABSTRACT

Embodiments are described herein for determining anatomical landmarks on a patient by virtue of anatomical landmarks being called up from a database with an anatomical model and being converted into individual body dimensions and an individual position of the patient. As a result, anatomical landmarks may be called up from a database, calculated individually for the patient and used as an item of reference location information. The positioning of the patient table is thus considerably accelerated, wherein the accuracy is also improved. Thus, the item of reference location information may be calculated individually for the same patient in a different position or a different patient with different body dimensions by virtue of this item of reference location information being recalculated by the conversion rule for the respective patient.

22 Claims, 2 Drawing Sheets

(51) Int. Cl.
*A61B 6/00* (2006.01)
*G06F 3/0482* (2013.01)
*G06F 19/00* (2018.01)
*G16H 30/00* (2018.01)

(52) U.S. Cl.
CPC ............ *A61B 6/467* (2013.01); *G06F 3/0482* (2013.01); *G06F 19/00* (2013.01); *G16H 30/00* (2018.01)

(56) References Cited

U.S. PATENT DOCUMENTS

| | | | | |
|---|---|---|---|---|
| 6,671,538 | B1* | 12/2003 | Ehnholm | A61B 90/10 382/131 |
| 7,170,967 | B2* | 1/2007 | Cherek | A61B 6/0457 378/20 |
| 7,308,075 | B2* | 12/2007 | Barkow | A61B 6/04 378/20 |
| 7,433,503 | B2* | 10/2008 | Cherek | A61B 5/0555 378/4 |
| 2002/0065461 | A1* | 5/2002 | Cosman | A61B 6/5247 600/426 |
| 2002/0118280 | A1* | 8/2002 | Medlar | A61B 6/08 348/77 |
| 2005/0228250 | A1* | 10/2005 | Bitter | A61B 5/02007 600/407 |
| 2011/0154569 | A1* | 6/2011 | Wiggers | A61B 6/0407 5/81.1 R |
| 2013/0136228 | A1* | 5/2013 | Lee | A61B 6/44 378/20 |
| 2014/0016750 | A1* | 1/2014 | Kang | A61B 6/547 378/62 |

* cited by examiner

AUTOMATED POSITIONING OF A PATIENT TABLE RELATIVE TO A MEDICAL INSTALLATION

CROSS-REFERENCE TO RELATED APPLICATIONS

This application claims the benefit of DE 10 2014 218 557.2, filed on Sep. 16, 2014, which is hereby incorporated by reference in its entirety.

TECHNICAL FIELD

The embodiments relate to a method and a user interface for the automated positioning of a patient table relative to a medical installation. The medical installation is, for example, a radiological imaging installation such as a computed tomography (CT) scanner or a C-arm X-ray machine, or an installation for irradiating a patient, (e.g., a medical linear accelerator).

BACKGROUND

The positioning of a patient table will be explained below using the example of a radiological examination; however, it is equally required for the use of other medical installations. For the planning of a radiological examination, for example, using computed tomography, a topogram of the area under examination is established. The topogram is the basis of the anatomical planning for the subsequent diagnostic scan. Furthermore, various parameters for automated optimization of an examination log may be derived from the topogram.

Positioning of an image capture area (also referred to as scan area) may at present take place by manual selection of a start line and an end line of the image capture area marked by a light beam localizer with laser marking lines on a patient or examination subject who or that is lying on a patient table of the installation movable in the longitudinal direction (e.g., z direction) relative to a scanner (e.g., the gantry of a CT scanner). The longitudinal axis of the patient may be parallel to the longitudinal direction of the patient table, and the patient table may be located outside the scanner. The start line and end line in this case extend in the width direction (e.g., x direction) of the patient table, as a result of which the image capture area is defined in the longitudinal direction of the patient.

In order to produce the topogram, the patient assumes a suitable position on the patient table. The operating personnel moves the table using driver commands into a suitable start position in order to capture an image of the organ or body region under examination. The start position is reached when the desired anatomical start point comes into alignment with a laser line in the gantry. In this case, the laser line marks the plane in which the scan begins.

It is known to compensate for positioning that is still imprecise at the beginning by manual readjustment by horizontal table movements. In this case, the operating personnel visually monitors, using a laser light beam localizer, whether the desired position in the scan plane has been reached.

DE 10 2007 017 794 B3 discloses an apparatus for the automated positioning of a patient table relative to a medical installation, which apparatus has a display and operating unit designed for outputting a patient image. The apparatus is designed for defining at least one item of reference location information on the patient table whilst simultaneously representing the item of reference location information in the patient image, as well as for subsequently moving the patient table with the aid of a positioning system, wherein the item of reference location information is brought into alignment with an image capture area of the medical installation.

SUMMARY AND DESCRIPTION

The scope of the present invention is defined solely by the appended claims and is not affected to any degree by the statements within this summary. The present embodiments may obviate one or more of the drawbacks or limitations in the related art.

An object of the present embodiments includes providing a user interface and a method for automated positioning of a patient table relative to a medical installation that enable precise and quick positioning.

This object is achieved by a user interface provided with a display and operating unit designed for outputting a patient image. The user interface furthermore includes a microprocessor programmed for defining at least one item of reference location information on the patient table and representing the item of reference location information in the patient image, and moving the patient table or the medical installation with the aid of a positioning system, wherein the item of reference location information is brought into alignment with a zero point of a working area of the medical installation.

The user interface is characterized by the fact that the microprocessor is programmed for storing the item of reference location information in an electronic memory, calling up the item of reference location information from the electronic memory at a later time, and re-moving the patient table or the medical installation with the aid of the positioning system, wherein the item of reference location information is again brought into alignment with the zero point of the working area of the medical installation.

In the method, a display and operating unit outputs a patient image. A microprocessor defines at least one item of reference location information on the patient table and represents this item of reference location information in the patient image. In addition, the microprocessor moves the patient table or the medical installation with the aid of a positioning system, wherein the item of reference location information is brought into alignment with a zero point of a working area of the medical installation.

The method is characterized by the fact that the microprocessor stores the item of reference location information in an electronic memory, calls up the item of reference location information at a later time from the electronic memory, and moves the patient table or the medical installation again with the aid of the positioning system, wherein the item of reference location information is again brought into alignment with the zero point of the working area of the medical installation.

The item of reference location information includes, for example, the coordinates of a point in a two-dimensional or three-dimensional space. The item of reference location information may also have a two-dimensional or three-dimensional extent and may represent, for example, a scan area, an irradiation area, or position and dimensions of an organ. In this case, a center point or boundary point of the item of reference location information is brought into alignment with the zero point of the working area of the medical installation.

The zero point of the working area of the medical installation is, for example, a zero point of an image capture area of a computed tomograph, or the center point of a region irradiated by a medical linear accelerator. The zero point may therefore be understood as the reference point or working point of the medical installation. It may be preset, for example, by coordinates in the two-dimensional or three-dimensional space.

The patient image is, for example, a two-dimensional or three-dimensional map of a real patient or a virtual avatar, which is output two-dimensionally or three-dimensionally on the display and operating unit.

The microprocessor is, for example, arranged in the display and operating unit, on a server or in a cloud and may also include a plurality of processors at different locations, which processors jointly implement identical or different acts of the method.

The method and the user interface make it possible to define one or more items of reference location information in the patient image that may be used as markers for table positioning and may be reactivated again and again. The item of reference location information is therefore a fixed reference point, in contrast to the definition of an only temporary start point in the patient image known from DE 10 2007 017 794 B3. The user interface and the method in this case make it possible to define any desired number of clinically relevant markers as items of reference location information on the patient image.

The user interface and the method provide, with the item of reference location information, a marker that does not have to be stored in the positioning system only once the correct table position has been reached but may be defined in advance in the patient image even before the patient table is moved to the corresponding position. The item of reference location information may therefore be defined purely on the basis of the patient image (and possibly on the basis of additional items of information that may be called up from databases). Furthermore, any desired number of items of reference location information may be set as markers. These may be called up again for follow-up examinations. In addition, the item of reference location information may be placed practically at any body position in the patient image. The item of reference location information represents a fixed target point for the travel of the patient table that may be approached again and again.

In accordance with one embodiment, the item of reference location information is defined with the display and operating unit on the basis of at least one user interaction that positions the item of reference location information in the patient image.

In order to implement this embodiment, a function for setting the item of reference location information is called up on the display and operating unit, for example. A user then positions the item of reference location information, for example, by moving the tip of a finger on a touchscreen, until the item of reference location information in the patient image is located at a clinically relevant point. Alternatively, the item of reference location information in the patient image may be set on the basis of the present position of the patient table.

The defining of the item of reference location information in the patient image is intuitive and quick for a user since the relevant point does not first need to be approached with the patient table and manually readjusted. Furthermore, in many cases, there is improved accuracy in the positioning, as a result of which readjustment may largely be dispensed with. The procedure is mentally less demanding and less tiring for the user.

In one development, the microprocessor calls up a representation of an avatar from the electronic memory and outputs this representation as patient image on the display and operating unit.

In accordance with one embodiment, at least one camera is oriented onto the patient table and captures the patient image.

For example, this may be a 3D camera that may scan the patient in three dimensions. A 2D camera or a plurality of cameras and/or depth sensors may also be used. The camera makes it possible to define the item of reference location information individually for each patient since the camera image of precisely this patient is output on the display and operating unit as patient image.

In one development, the microprocessor determines individual body dimensions and/or an individual position of limbs of the body of a patient on the patient table by evaluation of the patient image. The microprocessor furthermore calculates a conversion rule on the basis of a difference between the individual body dimensions of the patient and body dimensions in an anatomical model, and/or on the basis of a difference between the individual position of the limbs of the body of the patient and a position of body limbs in the anatomical model. Furthermore, the microprocessor converts coordinates between items of location information based on the anatomical model and items of patient-specific location information with the aid of the conversion rule.

This development makes it possible to determine anatomical landmarks on the patient by virtue of these anatomical landmarks being called up from a database with an anatomical model and being converted for the individual body dimensions and the individual position of the patient. As a result, anatomical landmarks may be called up from a database, calculated individually for the patient, and used as an item of reference location information. The positioning of the patient table is thus considerably accelerated, with the accuracy also being improved.

In accordance with one embodiment, the microprocessor calls up a plurality of items of anatomical location information, where each item specifies a position of an organ or a section of an organ in the anatomical model, from an anatomical database. The microprocessor converts each item of anatomical location information into an item of patient-specific anatomical location information with the aid of the conversion rule. Furthermore, the microprocessor stores each item of patient-specific anatomical location information as an item of reference location information in the electronic memory.

This embodiment makes it possible to produce the items of reference location information from algorithmically identified, anatomical landmarks from an anatomical model. Since each item of reference location information is now produced from an anatomical landmark, it no longer needs to be defined exclusively as the position of the patient table, but may be recalculated in each case. Thus, the item of reference location information may be calculated individually for the same patient in a different position or a different patient with different body dimensions by virtue of the item of reference location information being recalculated by the conversion rule for the respective patient. As a result, there is no need for the complexity involved in readjustment of the patient table, as a result of which the positioning is further accelerated. In this way, it is also possible to use the item of reference location information for follow-up examinations, as a result of which the corresponding anatomical area may be positioned precisely again, for example, for a plurality of therapeutic irradiations and/or radiological examinations.

In one development, the microprocessor defines the item of reference location information with the display and operating unit on the basis of at least one user interaction that positions the item of reference location information in the patient image. Then, the microprocessor converts the item of reference location information into a transformed item of location information based on the anatomical model by the conversion rule. Now, the microprocessor calls up an adjacent item of anatomical location information, which specifies a position of an organ or a section of an organ in the anatomical model, from the anatomical database, wherein the adjacent item of anatomical location information, among all the items of location information in the anatomical database, has the shortest distance from the transformed item of location information. Thereupon, the microprocessor links the item of reference location information with a name of the adjacent item of anatomical location information, and outputs the name on the display and operating unit.

This development makes it possible for the user to look up items of reference location information defined in the patient image in an anatomical database and to assign these items of reference location information to the respective anatomy, the name of which is thereupon output to the user. As a result, in addition to the image representation of the item of reference location information in the patient image, the user is also provided with a semantic designation for the item of reference location information, (e.g., "sternum"). As soon as the item of reference location information has been looked up in the anatomical database, this item of reference location information may then also be recalculated individually for the same patient in a different position or another patient with different body dimensions by virtue of this item of reference location information being looked up in the anatomical database and being calculated for the respective patient by the conversion rule. As a result, complexity involved in readjustment of the patient table is in principle dispensed with, as a result of which the positioning is further accelerated.

In accordance with one embodiment, the microprocessor acquires an anatomical name with the display and operating unit on the basis of at least one user interaction with which the anatomical name is input or selected. The microprocessor calls up an item of anatomical location information from the anatomical database on the basis of the anatomical name. The microprocessor converts the item of anatomical location information into an item of patient-specific location information by the conversion rule. Additionally, the microprocessor stores the item of patient-specific anatomical location information as an item of reference location information in the electronic memory.

This embodiment makes it possible for the user to generate the item of reference location information by imputing its anatomical name, as a result of which the procedure is further accelerated.

In one development, a plurality of items of reference location information is stored in the electronic memory. The microprocessor represents the items of reference location information in the patient image and selects one of the items of reference location information depending on a user interaction on the display and operating unit.

This development makes it possible for the user to select the desired item of reference location information, for example, from a multiplicity of anatomical landmarks.

In accordance with one embodiment, the microprocessor moves the patient table or the medical installation after the selection of the item of reference location information with the aid of the positioning system, wherein the selected item of reference location information is brought into alignment with the zero point of the working area of the medical installation.

By virtue of this embodiment, the user may also directly bring about corresponding positioning by selecting the item of reference location information.

In one development, the item of reference location information is stored in an electronic patient file or in a scan log.

This enables the use of the item of reference location information in follow-up examinations or for later irradiation.

In accordance with one embodiment, the microprocessor converts the item of reference location information into a transformed item of location information based on the anatomical model by the conversion rule. The microprocessor stores the transformed item of location information in an electronic patient file or in a scan log.

This embodiment makes it possible to store the item of reference location information independently of the present position of the patient in an electronic patient file or independently of individual body dimensions of the patient in a scan log, as a result of which later use is enabled even in the case of a changed position of the patient or in the case of a different patient.

A computer program that implements the method when it is executed in the microprocessor is stored on the computer-readable data carrier.

The computer program implements the method while it is executed in the microprocessor.

BRIEF DESCRIPTION OF THE DRAWINGS

Exemplary embodiments are explained in more detail below with reference to a figure. In the figures, identical or functionally identical elements have been provided with the same reference symbols where not stated otherwise. In the figures.

DETAILED DESCRIPTION

In CT equipment, unnecessary exposure of the patient to radiation may be avoided. Therefore, irrespective of whether initially only an image capture area for a topogram or directly an image capture area for diagnostic imaging needs to be determined, this may be selected to be as small as possible. In this case, the region of interest (ROI) may nevertheless naturally be completed covered. For this, the user or operator of the installation is able to identify precisely which anatomical regions of the patient are being sensed by the present setting, e.g., whether the ROI is completely within the image capture area of the CT equipment. Erroneous setting results in X-ray radiation emitted unnecessarily to the patient, to be precise in both cases when the image capture area is considerably greater than the ROI and when the image capture area is smaller than the ROI since in this case the ROI is insufficiently mapped and the scan procedure needs to be repeated.

Figure 1:
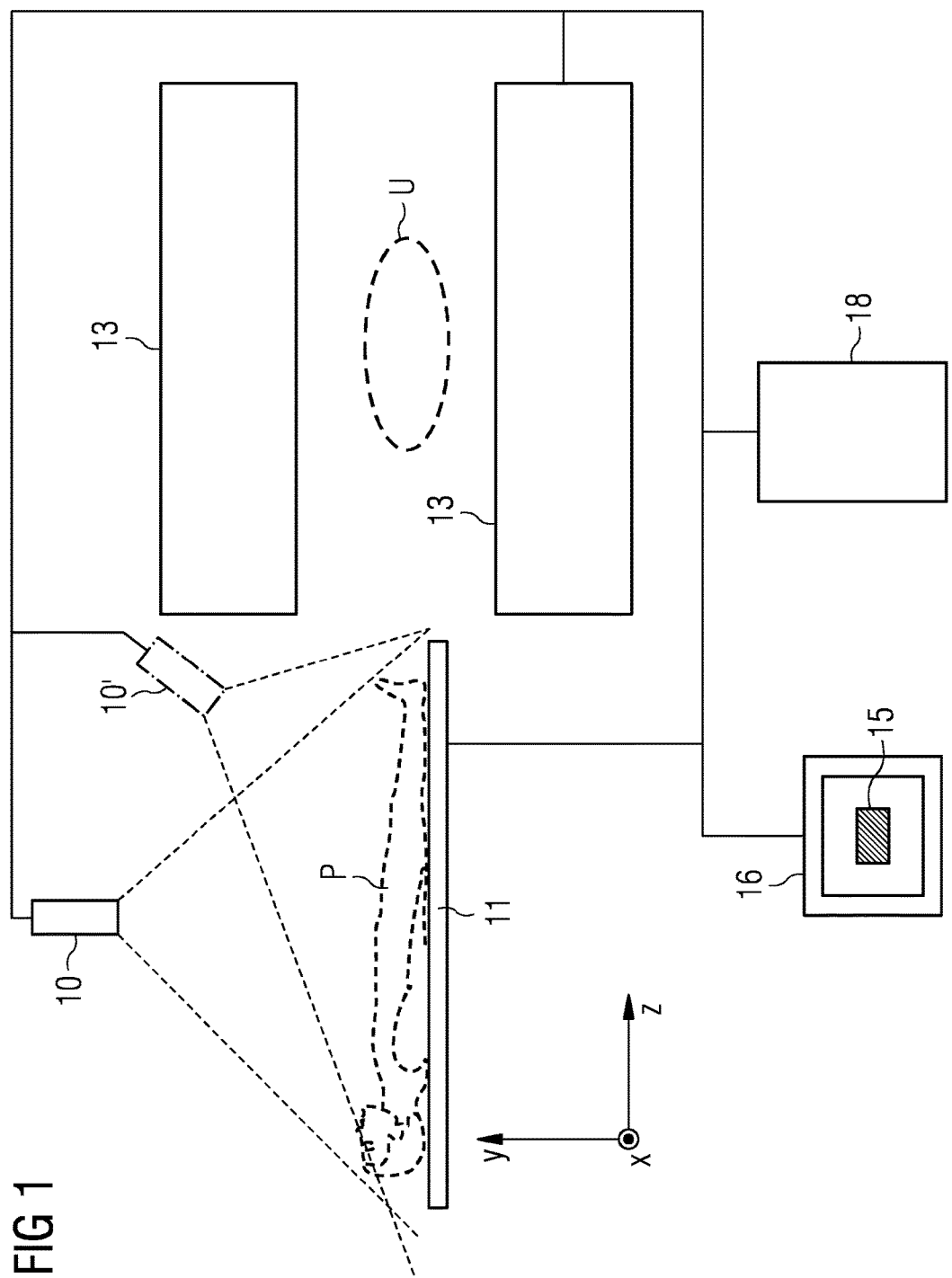
FIG. 1 depicts a schematic design of a user interface for the automated positioning of a patient table relative to a medical installation according to one example.

FIG. 1 depicts a schematic design of a user interface including a schematically illustrated medical installation 13, for example a magnetic resonance device, a computed tomography device or a medical linear accelerator having an investigation volume U (or irradiation area) with a known three-dimensional position and extent.

A movable patient table 11 with a patient P located thereon may be introduced into the medical installation 13. Alternatively, the medical installation 13 may be moved on rails over the patient table 11. A camera 10 for capturing a patient image 15 of the patient table 11 is assigned in three dimensions to the patient table 11 and is arranged perpendicularly over the patient table. A display and operating unit 16, which is connected to the camera 10 and the medical installation 13, is designed to display the patient image 15. An alternative camera 10' may be arranged on the medical installation 13 and oriented onto the patient table 11.

The display and operating unit 16 and a microprocessor 18, which is connected to or installed in the camera 10, the patient table 11, the medical imaging installation 13 and the display and operating unit 16 enable identification and/or verification of regions of the body under examination in the patient image 15. The microprocessor 18, in addition, determines the three-dimensional position of the identified body regions, calculates a movement path, and controls the movement of the patient table 11 or the medical installation 13 in the z direction in accordance with the calculated movement path.

The display and operating unit 16 is, for example, a personal computer or a workstation with a monitor, a keyboard and a mouse, a touchscreen or a tablet, which may also communicate wirelessly with the other components. The camera 10 may also be arranged to the side of the patient table 11.

The user interface depicted in FIG. 1 supplements the medical installation 13 by the camera 10, which permanently records the patient image 15 of the patient P or any other desired subject on the patient table 11. The camera image is passed on to the display and operating unit 16, where a user may view the patient image 15 and graphically define an item of reference location information that describes an area to be scanned.

The patient table 11 or the medical installation 13 is positioned in such a way that the item of reference location information is brought into alignment with the examination volume U. Additionally, the item of reference location information may be positioned at the edge of the examination volume U when the item of reference location information itself does not have an extent in the z direction but only defines a start line in the x or y direction or a start plane perpendicular to the z axis. For example, the item of reference location information is approached in such a way that it is brought into alignment with a laser line of a laser light beam localizer in a gantry of the medical installation 13.

By virtue of the item of reference location information being stored in an electronic memory, the item may be loaded again at a later point in time for repositioning. Instead of a camera image, a generic avatar representation may also be used as the patient image 15.

In one variant, the microprocessor 18 determines individual body dimensions and/or an individual position of limbs of the body of the patient P on the patient table 11 by evaluation of the patient image 15 and calculates a conversion rule on the basis of a difference between the individual body dimensions of the patient P and body dimensions in an anatomical model, and/or on the basis of a difference between the individual position of the limbs of the body of the patient P and a position of body limbs in the anatomical model. Thereupon, the microprocessor 18 uses this conversion rule to perform coordinate transformations between the anatomical model and the patient image 15, as required. Corresponding algorithms for the segmentation and position determination of body limbs are known from image processing, in particular, tracking of body movements and gestures. The conversion rule therefore makes it possible to correlate, using a suitable computer program, the patient image 15 with an anatomical model of the person so that dimensions and positions of organs may be calculated appropriately to the proportions of the respective patient P and may be visualized at the correct point in the patient image 15.

Furthermore, the microprocessor 18 may offer to the user a multiplicity of items of reference location information for selection on the display and operating unit 16 that it has taken as items of anatomical location information that each specify a position of an organ or a section of an organ in the anatomical model from an anatomical database and has then converted into items of patient-specific location information or into coordinates of the patient image 15. By virtue of the user selecting one of these items of reference location information on the display and operating unit 16, the patient table 11 may be brought immediately into the corresponding position.

Furthermore, the microprocessor 18 may also look up an item of reference location information positioned by the user on the display and operating unit 16 in the anatomical database and output the name of the corresponding organ to the user. If nothing else anatomical landmarks that have been input texturally or selected by the user may also be looked up in the anatomical database in this way, converted into items of patient-specific location information or into the coordinates of the patient image 15 and stored there as items of reference location information. Furthermore, electronic patient files and work logs of the medical installations used may be used as the storage location for the items of reference location information in patient-specific fashion in the coordinates of the patient image 15 or universally in the coordinates of the anatomical model.

Figure 2:
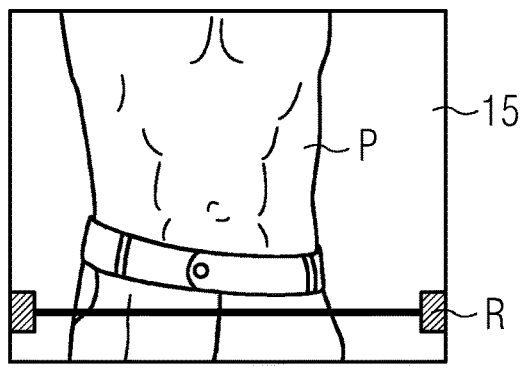
FIG. 2 depicts an example of an item of reference location information represented on a patient image.

FIG. 2 depicts a patient image 15 of a patient P on which an item of reference location information R for defining a start line of an area to be scanned is superimposed. By a user interaction, the user may move the item of reference location information R, in this case a horizontal line with touch points over the patient image 15. This user interaction is implemented, for example, using a keyboard or a mouse on a personal computer that the patient image 15. It may also take place, for example, by a touch input on a touchscreen, which outputs the patient image 15. Thus, the user may move the item of reference location information R by touching and dragging to the position desired by the user.

Figure 3:
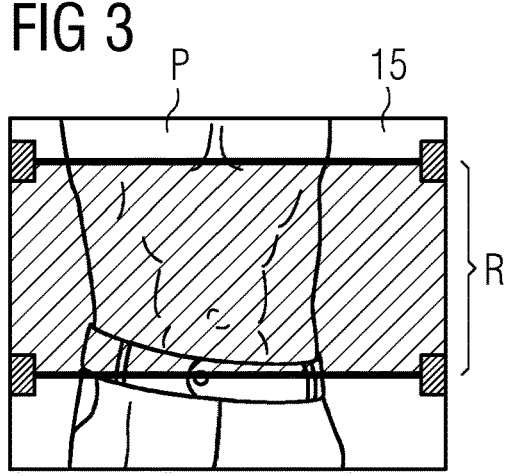
FIG. 3 depicts an example of an image capture area represented at an item of reference location information on a patient image.

FIG. 3 depicts a further variant of the item of reference location information R. In this case, the item of reference location information R in the patient image 15 of the patient P is represented as a hatched area bounded by two horizontal boundary lines. The horizontal lines are again provided with touch points that make it possible for a movement in the vertical direction to be performed conveniently by a mouse or touch input. The item of reference location information R is therefore positioned by a movable positioning graphical element.

Figure 4:
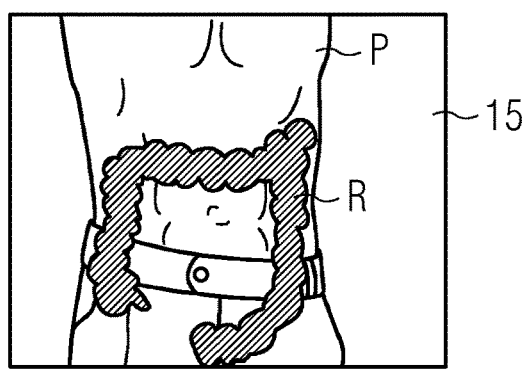
FIG. 4 depicts an example of an organ represented as an item of reference location information on a patient image.

FIG. 4 depicts that the item of reference location information R may also be represented quite differently. For example, in FIG. 4, the item of reference location information R is superimposed in the patient image 15 as a visualization of an organ of the patient P, (e.g., the colon of the patient P).

By virtue of a user interaction, for example, a speech command or an input by a keyboard, mouse, or touch, the user may now also select other organs as an item of reference location information R in order and represent them in the patient image 15.

As a deviation from the above-described exemplary embodiments, the item of reference location information R does not necessarily need to be represented as a line, organ, or area in a two-dimensional space. Other examples for visualization are points in a two-dimensional or three-dimensional space and planes or volumes in a three-dimensional space that may extend parallel to section planes of the medical installation.

The item of reference location information R may be represented in the form of a solid or multiply interrupted start line and/or end line projected virtually onto the patient in analogy to a light or laser marking. The item of reference location information R may relate, inter alia, to the start line, to the end line, or to both or to the image capture area spanned thereby.

The item of reference location information R may be stored in an electronic memory, for example, a main memory or a read-only memory. In this case, a multiplicity of items of reference location information R for the same or for different patients may also be stored.

The component parts or assemblies of the user interface are connected to one another in signal-conducting fashion in a suitable manner in order to be able to interact corresponding to the method. In this case, "signal-conducting" not only refers to an electrically conductive connection, but also any desired wireless link. In particular, the component parts or assemblies may also be connected to one another via a bus system.

Finally, reference is once again made to the fact that the method described above in detail and the user interface illustrated are merely exemplary embodiments that may be modified in a wide variety of ways by a person skilled in the art without departing from the scope of the featured embodiments. Although the embodiments have been described for use on a computed tomography scanner, for example, this does not exclude advantageous use for other medical installations. Other medical installations include, for example, (1) other X-ray-based installations, e.g., for producing conventional X-ray images or fluoroscopy; (2) magnetic resonance tomography (MRT) devices; (3) installations for producing images on the basis of radionuclides, e.g., scintigraphy, positron emission tomography (PET), single-photon emission computed tomography (SPECT); (4) installations for producing images on the basis of ultrasound waves, e.g., sonography, color dopplers; (5) installations for producing images on the basis of infrared radiation, e.g., diagnostic thermography; (6) installations for producing images on the basis of electric resistances or impedances, e.g., electrical impedance tomography (EIT); (7) installations for producing images on the basis of visible light, e.g., endoscopy, optical tomography; or (8) installations for therapeutically irradiating regions of the body of a patient, e.g., medical linear accelerators.

Furthermore, the use of the indefinite article "a" or "an" does not exclude that the relevant features may also be provided in multiple form. Likewise, the terms "unit" and "module" do not exclude the fact that the relevant components include a plurality of interacting partial components that may also be distributed in three dimensions, if appropriate.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing may be constructed to implement one or more of the methods or functionality as described herein.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and anyone or more processors of any kind of digital computer. A processor may receive instructions and data from a read only memory or a random access memory or both. Elements of a computer include a processor for performing instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device. Computer readable media suitable for storing computer program instructions and data include all forms of non-volatile memory, media and memory devices, including by way of example semiconductor memory devices, e.g., E PROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A user interface for automated positioning of a patient table relative to a medical installation, the user interface comprising:
   a display and operating unit configured to output a patient image; and
   a microprocessor configured to:
      define at least one item of reference location information on the patient table, wherein the at least one item of reference location information is a fixed reference point configured to be used as a marker for table positioning for moving and re-moving the patient table;
      represent the at least one item of reference location information in the patient image;
      move the patient table or the medical installation with aid of a positioning system, wherein the at least one item of reference location information is brought into alignment with a zero point of a working area of the medical installation;
      store, in an electronic memory, the at least one item of reference location information independently of a present position of a patient in an electronic patient file or independently of individual body dimensions of the patient in a scan log,
      call up the at least one item of reference location information from the electronic memory at a later time, and
      re-move the patient table or the medical installation with the aid of the positioning system, wherein the at least one item of reference location information is again brought into alignment with the zero point of the working area of the medical installation.

2. The user interface as claimed in claim 1, wherein the microprocessor is further configured to define the at least one item of reference location information with the display and operating unit based on at least one user interaction suitable for positioning the at least one item of reference location information in the patient image.

3. The user interface as claimed in claim 1, wherein the microprocessor is further configured to call up a representation of an avatar from the electronic memory and output the representation of the avatar as the patient image on the display and operating unit.

4. The user interface as claimed in claim 1, further comprising:
   at least one camera oriented onto the patient table and configured to capture the patient image.

5. The user interface as claimed in claim 4, wherein the microprocessor is further configured to:
   determine the individual body dimensions, an individual position of limbs, or the individual body dimensions and the individual position of the limbs of a body of the patient on the patient table by evaluation of the patient image;
   calculate a conversion rule based on one or more of (1) a difference between the individual body dimensions of the patient and body dimensions in an anatomical model or (2) a difference between the individual position of the limbs of the body of the patient and a position of body limbs in the anatomical model; and
   convert coordinates between items of location information based on the anatomical model and items of patient-specific location information with aid of the conversion rule.

6. The user interface as claimed in claim 5, wherein the microprocessor is further configured to:
   call up a plurality of items of anatomical location information, wherein each item of anatomical location information specifies a position of an organ or a section of an organ in the anatomical model from an anatomical database;
   convert each item of anatomical location information into an item of patient-specific anatomical location information with the aid of the conversion rule; and
   store each item of patient-specific anatomical location information as an item of reference location information in the electronic memory.

7. The user interface as claimed in claim 5, wherein the microprocessor is further configured to:
   define the at least one item of reference location information with the display and operating unit based on at least one user interaction suitable for positioning the at least one item of reference location information in the patient image;
   convert the at least one item of reference location information into a transformed item of location information based on the anatomical model by the conversion rule;
   call up an adjacent item of anatomical location information, which specifies a position of an organ or a section of an organ in the anatomical model from the anatomical database, wherein the adjacent item of anatomical location information, among all items of location information in the anatomical database, has a shortest distance from the transformed item of location information;
   link the at least one item of reference location information with a name of the adjacent item of anatomical location information; and
   output the name on the display and operation unit.

8. The user interface as claimed in claim 5, wherein the microprocessor is further configured to:
   detect an anatomical name with the display and operating unit based on at least one user interaction suitable for inputting or selecting the anatomical name;
   call up an item of anatomical location information from the anatomical database based on the anatomical name;
   convert the item of anatomical location information into an item of patient-specific location information by the conversion rule; and
   store the item of patient-specific anatomical location information as an item of reference location information in the electronic memory.

9. The user interface as claimed in claim 1, wherein a plurality of items of reference location information is stored in the electronic memory, and
   wherein the microprocessor is further configured to represent the plurality of items of reference location information in the patient image and select one item of reference location information of the plurality of items of reference location information depending on a user interaction on the display and operating unit.

10. The user interface as claimed in claim 9, wherein the microprocessor is further configured to move the patient table or the medical installation after selection of the item of reference location information with the aid of the positioning system, wherein the selected item of reference location information is brought into alignment with the zero point of the working area of the medical installation.

11. A method for automated positioning of a patient table relative to a medical installation, the method comprising:
outputting a patient image using a display and operating unit of a user interface;
defining, using a microprocessor of the user interface, at least one item of reference location information on the patient table and representing the at least one item of reference location information in the patient image, wherein the at least one item of reference location information is a fixed reference point configured to be used as a marker for table positioning for moving and re-moving the patient table;
moving the patient table or the medical installation, using the microprocessor, with aid of a positioning system, wherein the at least one item of reference location information is brought into alignment with a zero point of a working area of the medical installation;
storing, in an electronic memory using the microprocessor, the at least one item of reference location information independently of a present position of a patient in an electronic patient file or independently of individual body dimensions of the patient in a scan log;
calling up the at least one item of reference location information, using the microprocessor, at a later time from the electronic memory; and
moving the patient table or the medical installation again, using the microprocessor, with the aid of the positioning system, wherein the at least one item of reference location information is again brought into alignment with the zero point of the working area of the medical installation.

12. The method as claimed in claim 11, further comprising:
defining the at least one item of reference location information, using the microprocessor, with the display and operating unit based on at least one user interaction that positions the at least one item of reference location information in the patient image.

13. The method as claimed in claim 11, further comprising:
calling up a representation of an avatar, using the microprocessor, from the electronic memory; and
outputting the representation of the avatar as the patient image on the display and operating unit.

14. The method as claimed in claim 11, further comprising:
orienting at least one camera onto the patient table and capturing the patient image.

15. The method as claimed in claim 14, further comprising:
determining, using the microprocessor, individual body dimensions, an individual position of limbs, or the individual body dimensions and the individual position of the limbs of a body of the patient on the patient table by evaluation of the patient image;
calculating a conversion rule, using the microprocessor, based on one or more of: (1) a difference between the individual body dimensions of the patient and body dimensions in an anatomical model or (2) a difference between the individual position of the limbs of the body of the patient and a position of body limbs in the anatomical model; and
converting coordinates, using the microprocessor, between items of location information based on the anatomical model and items of patient-specific location information with aid of the conversion rule.

16. The method as claimed in claim 15, further comprising:
calling up a plurality of items of anatomical location information, using the microprocessor, wherein each item specifies a position of an organ or a section of an organ in the anatomical model from an anatomical database;
converting each item of anatomical location information, using the microprocessor, into an item of patient-specific anatomical location information with the aid of the conversion rule; and
storing each item of patient-specific anatomical location information, using the microprocessor, as an item of reference location information in the electronic memory.

17. The method as claimed in claim 15, further comprising:
defining the at least one item of reference location information, using the microprocessor, with the display and operating unit based on at least one user interaction that positions the at least one item of reference location information in the patient image;
converting the at least one item of reference location information, using the microprocessor, into a transformed item of location information based on the anatomical model by the conversion rule;
calling up an adjacent item of anatomical location information, using the microprocessor, wherein the adjacent item of anatomical location information specifies a position of an organ or a section of an organ in the anatomical model from the anatomical database, and wherein the adjacent item of anatomical location information, among all the items of location information in the anatomical database, has a shortest distance from the transformed item of location information;
linking the at least one item of reference location information, using the microprocessor, with a name of the adjacent item of anatomical location information; and
outputting the name on the display and operating unit.

18. The method as claimed in claim 15, further comprising:
acquiring an anatomical name, using the microprocessor, with the display and operating unit based on at least one user interaction with which the anatomical name is input or selected;
calling up an item of anatomical location information, using the microprocessor, from the anatomical database based on the anatomical name;
converting the item of anatomical location information, using the microprocessor, into an item of patient-specific location information by the conversion rule; and
storing the item of patient-specific anatomical location information, using the microprocessor, as an item of reference location information in the electronic memory.

19. The method as claimed in claim 15, further comprising:
converting the at least one item of reference location information, using the microprocessor, into a transformed item of location information based on the anatomical model by the conversion rule; and
storing the transformed item of location information, using the microprocessor, in an electronic patient file or in a scan log.

20. The method as claimed in claim 11, further comprising:
- storing a plurality of items of reference location information in the electronic memory; and
- representing the plurality of items of reference location information, using the microprocessor, in the patient image; and
- selecting, using the microprocessor, one item of reference location information of the plurality of items of reference location information depending on a user interaction on the display and operating unit.

21. The method as claimed in claim 20, further comprising:
- moving the patient table or the medical installation, using the microprocessor, after the selection of the item of reference location information with the aid of the positioning system, wherein the selected item of reference location information is brought into alignment with the zero point of the working area of the medical installation.

22. The method as claimed in claim 11, further comprising:
- storing the at least one item of reference location information, using the microprocessor, in an electronic patient file or in a scan log.

* * * * *